United States Patent [19]
Hobbs

[11] Patent Number: 5,853,749
[45] Date of Patent: Dec. 29, 1998

[54] GEL WOUND DRESSING

[75] Inventor: Tracey Susan Hobbs, Swindon, Great Britain

[73] Assignee: Scimat Limited, Great Britain

[21] Appl. No.: 776,481

[22] PCT Filed: Jul. 31, 1995

[86] PCT No.: PCT/GB95/01804

§ 371 Date: Mar. 31, 1997

§ 102(e) Date: Mar. 31, 1997

[87] PCT Pub. No.: WO96/15368

PCT Pub. Date: Feb. 15, 1996

[30]     Foreign Application Priority Data

Jul. 30, 1994 [GB] United Kingdom ................ 9415739.3

[51] Int. Cl.⁶ ........................ A61K 31/74; A61L 15/16
[52] U.S. Cl. ................ 424/443; 424/78.01; 424/78.03; 424/78.06; 424/445; 424/446
[58] Field of Search ................. 424/443, 78.01, 424/78.03, 78.06, 445, 446, 447, 449

[56]     References Cited

U.S. PATENT DOCUMENTS

| | | | |
|---|---|---|---|
| 3,957,605 | 5/1976 | Assarsson et al. | 204/159.14 |
| 4,076,663 | 2/1978 | Masuda et al. | 260/17.4 GC |
| 4,226,232 | 10/1980 | Spence | 128/156 |
| 4,302,369 | 11/1981 | Elmquist | 260/17.4 GC |
| 4,781,919 | 11/1988 | Liebowitz | 424/78 |
| 5,505,718 | 4/1996 | Roe et al. | 604/368 |

FOREIGN PATENT DOCUMENTS

| | | |
|---|---|---|
| EP 0 100 458 | 2/1984 | European Pat. Off. . |
| EP 0 157 960 | 10/1985 | European Pat. Off. . |
| EP 0 169 658 | 1/1986 | European Pat. Off. . |
| EP 0278 601 | 8/1988 | European Pat. Off. . |
| EP 0 280 737 | 9/1988 | European Pat. Off. . |
| EP 0 309 187 | 3/1989 | European Pat. Off. . |
| 0 509 708 | 10/1992 | European Pat. Off. . |
| 1512325 | 1/1978 | United Kingdom . |
| GB 2 048 292 | 12/1980 | United Kingdom . |
| GB 2 083 487 | 3/1982 | United Kingdom . |
| GB 2 156 370 | 10/1985 | United Kingdom . |
| WO91/15368 | 10/1991 | WIPO . |

OTHER PUBLICATIONS

Abstract–JP3141229 –"Composition and Drug for Treating Wound", Jun. 1991.

*Primary Examiner*—Thurman K. Page
*Assistant Examiner*—Kathryne E. Shelborne
*Attorney, Agent, or Firm*—Lerner, David, Littenberg, Krumholz and Mentlik

[57]     ABSTRACT

This invention relates to a gel wound dressing material, and to techniques for preparing and using such a material. The invention provides a gel wound dressing in which the polymer component comprises a copolymer of a starch and a monounsaturated carboxylic acid or an ester or salt thereof, the copolymer being in the form of particles of which at least 70% by weight have a size of not more than about 100 um; and water. 1.

26 Claims, No Drawings

GEL WOUND DRESSING

This application is a 35 USC 371 of PCT GB95/01804 filed Jul. 31, 1995.

This invention relates to a gel wound dressing material, and to techniques for preparing and using such a material.

It is desirable to control the condition of a wound to encourage the healing process by maintaining it sufficiently moist so as to absorb or to eliminate the formation of dry crusty tissue in the vicinity of the wound, while also absorbing materials exuded from the wound, including dead leucocytes, epidermal and dermal cells. At the same time, it is desirable to prevent access to the wound of agents, whether bacterial or fungal, which can lead to infection. Examples of wounds to which these factors are relevant are ulcers, traumatic and surgical wounds, and burns, and tissue donor sites.

Traditionally, wounds have been encouraged to heal by placing a gauze material over the wound. More recently, however, it has been proposed to apply a gel material over the wound. A suitable gel material is disclosed in U.S. Pat. No. 4,226,232. It comprises a hydrolysed copolymer of starch-and an acrylonitrile. The polymer is prepared in gel form by mixture with water, to an extent which gives the copolymer an appropriate viscosity which enables it to be manipulated as a gel, especially when applying it to a wound and while it is applied to the wound. Modified such materials are disclosed in U.S. Pat. No. 4,302,369, in which the polymer is converted to its aluminium salt to increase its ability to absorb solutions with a high ionic strength.

Appropriate properties for a gel, for use as a wound dressing include a viscosity that makes the material capable of being manipulated before administration to a wound and then applied appropriately over the area of the wound, and an ability to absorb exudate from the wound. The need to be able to manipulate a gel material for a wound dressing conveniently has to be balanced with the ability of the gel to absorb additional liquid; the mixture of the polymer with water to confer the gel viscosity on the polymer will result in a reduction of the ability of the polymer to absorb liquid.

The present invention provides a gel-wound dressing in which the polymer component comprises a copolymer of a starch and a monounsaturated carboxylic acid or an ester or salt thereof.

Accordingly, in one aspect, the invention provides a gel wound dressing which comprises:

(a) a water absorbent copolymer of a starch and a monounsaturated carboxylic acid or an ester or salt thereof; and (b) water.

The dressing material may further comprise a preservative or other additive.

The dressing of the invention has the advantage that it can be provided as a gel, and therefore be manipulated conveniently before application to a wound and while it is so applied, with an ability to absorb fluids which can be at least comparable with gel wound dressings based on other polymer systems. The dressing can also provide appropriate moisture levels to minimise the risk of a wound drying out during the healing process, which can itself give rise to complications in the healing process in terms of the formation of crusty tissue. The dressing material of the invention can be made with a viscosity which is at least about 100 kcps, preferably at least about 125 kcps, for example at least about 160 kcps. The viscosity can be arranged to be not more than about 300 kcps, more preferably not more than about 275 kcps, for example not more than about 250 kcps. The viscosity of the dressing material is measured on a Brookfield RVF viscometer with a helipath stand, using a T-bar D spindle at 4 rpm.

The viscosities referred to above can be attained according to the present invention while maintaining a high ability to absorb exuded materials from the wound as can be demonstrated by means of a saline absorption test. That test comprises dispersing 2 g of the dressing material in 20 ml of 0.9% aqueous NaCl solution. The dispersion is decanted into a 50 ml measuring cylinder. Once the dispersion has settled, the position of the phase separation is noted from which the fluid absorption capacity can be calculated. It has been found that the dressing material of the invention can be made with a viscosity within the limits mentioned above, with a saline absorption of at least about 200 ml of the solution per 100 g of the wound dressing, preferably at least about 250 ml.100 $g^{-1}$, more preferably at least about 300 ml.100 $g^{-1}$. The absorption characteristics of the dressing material have been found to be enhanced as a result of a sterilisation step in its preparation which involves exposing the material to heat and pressure. The viscosity that can be obtained in the material of the wound dressing material of the invention means that the material is capable of being manipulated conveniently over the area of the wound that is to be treated using the material. It also facilitates removal of the material from its packaging. In addition to facilitating manipulation, a relatively low viscosity can enable the tackiness of the material to be maintained relatively low, which reduces damage to the wound when the dressing is removed.

Control of the viscosity is one means of measurement which may be used to obtain a required ratio between copolymer and water in the gel mixture. However, other means may be adopted, to achieve desired water-absorption properties of the gel mixture, which effectively comprises required provision of a suitable "spreadable gel". This can range between "highly mobile" at one extreme to "very stiff" at the other extreme, and which can be obtained by variation of the proportion by weight of copolymer in the gel mixture between about 0.2% to about 6%. The particular weight proportion which may be selected can depend on the particular means adopted to dispense the gel mixture, with e.g. a highly mobile gel being suitable for introduction into a deep wound by a syringe, and a stiffer gel being suitable for extrusion e.g. from a squeezable sachet so as to be readily spread over the wound area.

In one preferred arrangement, the gel mixture may be stored in a squeezable sachet, and therefore the required properties of the gel mixture will be such that it can be readily be squeezed from the sachet, and to be readily spread over the wound area.

The gel wound dressing of the invention has been found to be capable of providing suitable absorption characteristics, in particular towards solutions which are high in ionic strength, without any need to include aluminium ions. This can represent a significant advantage, in particular in situations in which the presence of aluminium ions can give rise to clinical complications.

Preferably, the gel wound dressing is formed from a mixture of particles of the copolymer and water, in which the distribution of particles is such that at least about 70% by weight, more preferably at least about 80%, especially at least about 90%, have a particle size of not more than about 100 $\mu$m. Preferably, the gel wound dressing is formed from a mixture of particles of the copolymer and water, in which the distribution of particles is such that at least about 60% by weight, more preferably at least about 70%, especially at least about 85%, have a particle size of not more than about 75 μm. Preferably, the distribution of particles is such that not more than about 10% by weight, more preferably not more than about 6%, have a particle size greater than about 100 μm. The particle size distribution can be determined using sieves with known mesh sizes, as is known.

It has been found that the use of particles of the copolymer whose size satisfies some or all of these conditions gives rise to materials with viscosities which make the copolymer suitable for use in the treatment of wounds, with the characteristics of a gel. The use of particles of the polymer with a size within these ranges has the advantage of making the material smoother without a granular texture. The smooth texture makes the material easier to spread appropriately over a wound that is to be treated. Also the gel usually will be clear i.e. transparent, so that the wound can be observed while the dressing is being applied.

Preferably, the gel wound dressing of the invention includes a component which reduces its tendency to dry out. This component may also act as a preservative. Examples of suitable materials include polyols, such as propane-1,2-diol and glycerol, or a mixture thereof. Preferably, the polyol component is present in the composition in an amount of at least about 100% by weight based on the weight of the copolymer, more preferably at least about 200%, especially at least about 300%, for example about 400%, and with advantage even up to 600%.

Preferably, the gel wound dressing of the invention includes at least one other active component. For example, the dressing might include an agent which inhibits or at least reduces the tendency for bacteria to colonise on the dressing. An example of a suitable such agent is a polyol such as propane-1,2-diol.

Examples of other active components that might be included in the dressing include anaesthetic agents, hormonal compounds and lubricants, enzyme-containing compositions, antibiotics (such as metronidazole), collagen materials, cytokines (such as platelet derived growth factor, insulin-dependent growth factor, and transforming factored placentile growth factor), and elastin (preferably with fibrin and fibrinogen).

The copolymer used in the dressing is produced by reaction of a starch with a monoethylenically unsaturated carboxylic acid, or an ester or salt of such an acid. Examples of suitable components for the copolymer, together with the starch, include acrylic acid, methacrylic acid, lower carboxyl ($C_1$ to $C_4$) esters thereof and salts such as with elements of Groups I and II or ammonia. It is preferred that substantially all of the carboxyl groups in the copolymer are present as acid groups, or as salt or ester derivatives of acid groups.

A particularly preferred copolymer comprises at least about 50%, preferably at least about 70%, more preferably at least about 85%, for example at least about 95%, of a salt of a starch grafted polyacrylate. Preferred salts include toe sodium salt.

The copolymerisation reaction between the starch and the acrylate component can be initiated by means of irradiation, for example using an electron beam, γ-radiation such as from a $Co^{60}$ source, or ultraviolet radiation. The reaction can also be initiated by means of a chemical initiator such as benzoyl peroxide, hydrogen peroxide or a salt such as a ceric salt.

Examples of suitable copolymers for use in the gel wound dressing of the invention are disclosed in GB-1512325. Subject matter disclosed in that document is incorporated in the specification of this application by this reference. The document discloses a water absorbing resin which comprises a copolymer of starch and a water soluble monomer such as acrylic acid or a derivative thereof. The resin is crosslinked as a result of a reaction with a crosslinking agent such as polyesters of unsaturated mono- or polycarboxylic acids with polyols (for example an ester of di-methacrylic acid with ethylene glycol). The resin is said to be suitable for absorbing fluids such as blood and urine, for example in diapers, sanitary towels and disposable dustcloths for kitchens. The disclosed resin can be applied in the form of a powder, in an aqueous dispersion, or by immersion of a substrate in a solution of the resin. The resin is said to be particularly suitable for use in diapers and sanitary towels.

The copolymer used in the dressing of the invention will generally be crosslinked, so as to confer appropriate gel-like properties and viscosity on the dressing material. The crosslinks will preferably be internal crosslinks. It has been found that the use of a polymer which is crosslinked in this way gives rise to a smoother dressing material, which has advantages in use for example in terms of its ability to be spread.

The starch used to form the copolymer may be a natural starch such as potato starch, rice starch, tapioca starch or corn starch, or a modified or processed starch such as α-starch, dextrine and oxidised starch. Natural starches are particularly preferred.

The ratio by weight of the starch to the acid derivative component of the copolymer is preferably at least about 1, more preferably at least about 2, especially at least about 5, for example at least about 10. The ratio is preferably not more than about $10^4$, more preferably not more than about $10^3$, especially not more than about 100.

Suitable starch acrylate copolymers for use in the wound dressing of the invention are available from Hoechst Celanese under the trade mark SANWET COS-915.

Preferably, the water that is present in the wound dressing gel is not more than about 60% of the total water absorbency of the copolymer, more preferably not more than about 5%, for example not more than about 3%.

The water absorbency of the copolymer is determined by immersing in deionised water a known weight of the gel (1 to 2 g) made to the exemplified formulation, contained in a sealed bag of a hydrophilic polypropylene based non-woven fabric available from Scimat Limited under the trade mark SCIMAT 700/13, and recording its weight change after 24 hours.

Prior to weighing, the surface of the bag is blotted to remove excess water and an empty bag is used as a control.

The total absorbency of the resin, measured in $ml.g^{-1}$, is calculated as follows:

$$\text{Absorbency} = \frac{\text{(Water in gel)} + \text{(Water uptake in 24h)}}{\text{Resin in gel}}$$

However, the total water absorbency (T) can be difficult to measure in practice (due to variation between different batches of material), but tests carried out to date give the following desired parameters, wherein carrying out measurements for values from 900 to 1300 ml/g for pure water:

$$\text{In the formula: } R = \frac{Y}{xT} \times 100\%$$

in which R is the percentage proportion by weight of water present in the gel mixture relative to the total water absorbency of the copolymer in the gel mixture; T is the total water absorbency; x is the percentage by weight of copolymer in the copolymer/water gel mixture, and Y=amount of water added in the mixing stage.

For values of x=0.2 and T=900 and 1300 and Y=99.8, the values of R were found to be 55.4 and 38.4 respectively.

For value of x=6, and values of T=900 and T=1300 and Y=94, the values of R were found to be 1.74 and 1.21 respectively.

The value of x=0.2 gives a gel mixture which is very runny, or "highly mobile" as indicated earlier, whereas the value x=6.0 gives a gel mixture which is very stiff. These two values of x determine the range within which a suitable spreadable gel can be derived, to suit particular requirements. Therefore, suitable variation of the weight proportions of copolymer and water in the gel mixture may be selected, by experiment, within the range, to provide spreadable gel mixtures suitable for different requirements.

In a preferred example, which contains 3.5 parts copolymer and 75.5 parts water, then when T=900, R=2.4; and when T=1300, R=1.66, and Y=75.5.

Accordingly, in a particularly preferred range of proportion by weight of copolymer to water in a gel mixture of a gel wound dressing according to the invention, the relative proportion of water that is present in a particular sample, compared with the total water absorbency of the copolymer in the sample, lies in a range having a minimum value of up to 1.0%. The upper limit to the preferred range will be determined by experiment, but may go up to as high a value as R=60%.

If desired, for certain circumstances it may be advantageous to introduce substantial amounts of preservative e.g. a polyol into the gel mixture, (which replaces the amount of water required in the formulation of the gel), and this can then result in a lower value of R. By way of example, in a gel mixture of 3% polymer, 69% polyol, and 28% water, the value of R is reduced to 0.7. The invention therefore includes the possibility of including weight proportions in the gel mixture of polymer, preservative, and water such that R can be less than 1.0%, and down to at least 0.7%.

The gel dressing will generally be applied to a wound in a layer of thickness at least about 2 mm, preferably at least about 4 mm, for example at least about 5 mm. A dressing applied to certain wounds with this thickness can be left in situ for as much as seven days or more.

The dressing of the invention can be administered in a sachet from which it can be extruded through an opening, formed for example by means of a knife, by the application of pressure to the sachet.

The dressing can conveniently be administered in a syringe, from which it can be extruded in a controlled manner directly onto a wound so that it is appropriately located to ensure that the wetness of the wound is controlled.

The dressing can be administered in a porous container such as a pouch or sachet made of a material that is suitably porous to the fluids to be absorbed by the dressing when in place on the wound. Examples of materials that might be suitable for the sachet or pouch include paper based materials and organic materials such as polyamides and polyesters, especially in the form of a non-woven sheet.

The wound dressing of the invention can conveniently be applied directly to a wound. It is envisaged that, in most circumstances, the dressing will be changed after a period of, perhaps, hours or days, according to the condition of the wound, for example about 2 to 3 days (although shorter periods can be appropriate under certain conditions, for example when the amount of material exuding from the wound is high). When the dressing is to be changed, the gel-like characteristics of the dressing material facilitate its removal from the wound, and which may be assisted by irrigation, for example using a sterile saline solution.

It will generally be appropriate for a secondary dressing to be applied over the gel wound dressing, to retain it in place on a wound and to provide a degree of physical protection for the gel dressing. The nature of the secondary dressing will depend on the characteristics of the wound. For example, if the wound has eschar (dry crusty tissue) associated with it, a moisture vapour permeable dressing will be appropriate. If the wound is malodorous, an activated carbon dressing can be appropriate.

An appropriate secondary dressing can preferably exclude bacteria from the wound, retain the dressing material in place on the wound, and permit exchange of moisture with the atmosphere. Preferably, the dressing is transparent so that the wound can be inspected. Suitable secondary dressings are sold under the trade marks OPSITE and TEGADERM.

The invention also provides a method of making a gel wound dressing material, which comprises mixing a water absorbent copolymer of a starch and a monounsaturated carboxylic acid or an ester or salt thereof with a quantity of water, the proportions of the copolymer and water being such that the resulting mixture has gel properties.

Preferably, the method includes the step of sterilising the gel wound dressing, for example by means of a heating step, optionally under pressure, or by irradiation if the materials of the dressing are not affected adversely by irradiation. Unexpectedly the saline absorbency capacity of the sterilised gel is greater than that before sterilisation.

The invention further provides a method of treating a wound which includes the step of applying a gel wound dressing of the type discussed above.

An example of a gel wound dressing will now be described. The dressing was made from a starch acrylate copolymer sold under the trade mark SANWET COS-915. It is supplied by Hoechst Celanese. Typically it has a particle size distribution as follows:

We claim:

1. A gel wound dressing which comprises a mixture of:
   (a) a water absorbent copolymer of a starch and a monounsaturated carboxylic acid or an ester or salt thereof, the copolymer being in the form of particles of which at least about 70% by weight have a size of not more than about 100 $\mu$m; and
   (b) water.

2. A wound dressing as claimed in claim 1, which includes a component which reduces the tendency of the dressing to dry out when exposed to atmosphere.

3. A wound dressing as claimed in claim 2, in which the said component is a polyol.

4. A wound dressing as claimed in claim 3, in which the said component comprises propane-1,2-diol.

5. A wound dressing as claimed in claim 2, in which the said component is present in an amount of at least 100% based on the weight of the copolymer.

6. A wound dressing as claimed in claim 1, which includes an agent which inhibits or at least reduces the tendency for bacteria to colonise on the dressing.

7. A wound dressing as claimed in claim 1, in which the distribution of the particles of the copolymer is such that at least about 80% have a particle size of not more than about 100 $\mu$m.

8. A wound dressing as claimed in claim 1 in which substantially all of the carboxyl groups in the copolymer are present as acid groups, or as salt or ester derivatives of acid groups.

9. A wound dressing as claimed in claim 1, in which the wound dressing comprises a spreadable gel mixture.

10. A wound dressing as claimed in claim 1, in which the proportion by weight of copolymer lies in the range from 0.2 to 6%.

11. A wound dressing as claimed in claim 1, in which, in the formula:

$$R = \frac{Y}{xT} \times 100\%$$

where R is the percentage proportion by weight of water present in the mixture relative to the total water absorbency of the copolymer, T is the total water absorbency, x is the percentage by weight of copolymer and Y is the amount of water in the mixing stage, R is at least 0.7%.

12. A wound dressing as claimed in claim 11, in which R is not more than 60%.

13. A wound dressing as claimed in claim 1, which is contained in a sachet from which the dressing can be extruded by application of pressure.

14. A wound dressing as claimed in claim 7 in which the distribution of the particles of the copolymer is such that at least about 90% have a particle size of not more than about 100 μm.

15. A gel wound dressing contained in a syringe, the gel wound dressing comprising a mixture of:
  (a) a water absorbent polymer of a starch and a monosaturated carboxylic acid or an ester or salt thereof, the copolymer being in the form of particles of which at least about 70% by weight have a size of not more than about 100 μm; and
  (b) water.

16. A wound dressing as claimed in claim 15, including a component which reduces the tendency of the dressing to dry out when exposed to the atmosphere.

17. A wound dressing as claimed in claim 15, wherein said component comprises a polyol.

18. A wound dressing as claimed in claim 15, wherein said component comprises propane-1,2-diol.

19. A wound dressing as claimed in claim 15, wherein said component is present in an amount of at least 100% based on the weight of the copolymer.

20. A wound dressing as claimed in claim 15, including an agent which inhibits or at least reduces the tendency for bacteria to colonize on the dressing.

21. A wound dressing as claimed in claim 15, wherein the distribution of the particles of the copolymer is such that at least about 80% have a particle size of not more than about 100 μm.

22. A wound dressing as claimed in claim 15, wherein substantially all of the carboxyl groups in the copolymer are present as acid groups, or as salt or ester derivatives of said acid groups.

23. A wound dressing as claimed in claim 15, wherein said wound dressing comprises a spreadable gel mixture.

24. A wound dressing as claimed in claim 15, wherein the proportion by weight of copolymer lies in the range from 0.2 to 6%.

25. A wound dressing as claimed in claim 15, wherein, in the formula:

$$R = \frac{Y}{xT} \times 100\%$$

where R is the percentage proportion by weight of water present in the mixture relative to the total water absorbency of the copolymer, T is the total water absorbency, x is the percentage by weight of copolymer and Y is the amount of water in the mixing stage, R is at least 0.7%.

26. A wound dressing as claimed in claim 15, wherein R is not more than 60%.

* * * * *

UNITED STATES PATENT AND TRADEMARK OFFICE
CERTIFICATE OF CORRECTION

PATENT : 5,853,749

DATED : December 29, 1998

INVENTOR(S) : Tracey Susan Hobbs

It is certified that error appears in the above-identified patent and that said Letters Patent is hereby corrected as shown below:

Columns 1-8, should be deleted and substitute therefor columns 1-10, as shown on the attached pages.

Signed and Sealed this

Third Day of April, 2001

*Attest:*

NICHOLAS P. GODICI

*Attesting Officer*  *Acting Director of the United States Patent and Trademark Office*

GEL WOUND DRESSING

FIELD OF THE INVENTION

This invention relates to a gel wound dressing material, and to techniques for preparing and using such a material.

BACKGROUND OF THE INVENTION

It is desirable to control the condition of a wound to encourage the healing process by maintaining it sufficiently moist so as to absorb or to eliminate the formation of dry crusty tissue in the vicinity of the wound, while also absorbing materials exuded from the wound, including dead leucocytes, epidermal and dermal cells. At the same time, it is desirable to prevent access to the wound of agents, whether bacterial or fungal, which can lead to infection. Examples of wounds to which these factors are relevant are ulcers, traumatic and surgical wounds, burns, and tissue donor sites.

Traditionally, wounds have been encouraged to heal by placing a gauze material over the wound. More recently, however, it has been proposed to apply a gel material over the wound. A suitable gel material is disclosed in U.S. Pat. No. 4,226,232. It comprises a hydrolyzed copolymer of starch and an acrylonitrile. The polymer is prepared in gel form by mixture with water, to an extent which gives the copolymer an appropriate viscosity which enables it to be manipulated as a gel, especially when applying it to a wound and while it is applied to the wound. Modified such materials are disclosed in U.S. Pat. No. 4,302,369, in which the polymer is converted to its aluminum salt to increase it ability to absorb solutions with a high ionic strength.

Appropriate properties for a gel, for use as a wound dressing, include a viscosity that makes the material capable of being manipulated before administration to a wound and then applied appropriately over the area of the wound, and an ability to absorb exudate from the wound. The need to be able to manipulate a gel material for a wound dressing conveniently has to be balanced with the ability of the gel to absorb additional liquid; the mixture of the polymer with water to confer the gel viscosity on the polymer will result in a reduction of the ability of the polymer to absorb liquid.

SUMMARY OF THE INVENTION

The present invention provides a gel wound dressing in which the polymer component comprises a copolymer of a starch and a monounsaturated carboxylic acid or an ester or salt thereof.

In accordance with one embodiment of the present invention, there is provided a gel wound dressing which comprises:

(a) a water absorbent copolymer of a starch and a monounsaturated carboxylic acid or an ester or salt thereof; and (b) water.

The dressing material may further comprise a preservative or other additive.

In accordance with another embodiment of the present invention, there is provided a gel wound dressing which comprises a mixture of:

(a) a water absorbent copolymer of a starch and a monounsaturated carboxylic acid or an ester or salt thereof, the copolymer being in the form of particles of which at least about 70% by weight have a size of not more than about 100 μm; and (b) water.

In a preferred embodiment, the wound dressing includes a component which reduces the tendency of the dressing to dry out when exposed to atmosphere. Preferably, this component is a polyol, and most preferably propane-1,2-diol.

In accordance with another embodiment of the wound dressing of the present invention, a component is present in an amount of at least 100% based on the weight of the copolymer.

In accordance with another embodiment of the wound dressing of the present invention, the wound dressing includes an agent which inhibits or at least reduces the tendency for bacteria to colonize on the dressing.

In accordance with another embodiment to the wound dressing of the present invention, the distribution of the particles of the copolymer is such that at least about 80% have a particle size of not more than about 100 μm, and in particular, at least about 90% have a particle size of not more than about 100 μm.

In accordance with another embodiment of the wound dressing of the present invention, substantially all of the carboxyl groups in the copolymer are present as acid groups, or a salt or ester derivative of acid groups.

In accordance with another embodiment of the wound dressing of the present invention, the wound dressing comprises a spreadable gel mixture.

In accordance with another embodiment of the wound dressing of the present invention, the proportion by weight of copolymer lies in the range of from about 0.2 to 6%.

In accordance with another embodiment of the wound dressing of the present invention, in the formula $$R = \frac{Y}{xT} \times 100\%$$

where R is percentage proportion by weight of water present in the mixture relative to the total water absorbency of the copolymer, T is the total water absorbency, x is the percentage by weight of copolymer and Y is the amount of water in the mixing stage, R is at least about 0.7% Preferably, R is not more than 60%.

In accordance with another embodiment of the wound dressing of the present invention, the wound dressing is contained in a syringe. In another embodiment, the wound dressing is contained is a sachet from which the dressing can be extruded by application of pressure thereto.

DETAILED DESCRIPTION

The dressing of the present invention has the advantage that it can be provided as a gel, and therefore it can be provided as a gel, and therefore it can be manipulated conveniently before application to a wound and while it is so applied, with an ability to absorb fluids which can be at least comparable with gel wound dressings based on other polymer systems. The dressing can also provide appropriate moisture levels to minimize the risk of a wound drying out during the healing process, which can itself give rise to complications in the healing process in terms of the formation of crusty tissue. The dressing material of the invention can be made with a viscosity which is at least about 100 kcps, preferably at least about 125 kcps, for example at least about 160 kcps. The viscosity can be arranged to be not more than about 300 kcps, more preferably not more than about 275 kcps, for example not more than about 250 kcps. The viscosity of the dressing material is measured on a Brookfield RVF viscometer with a helipath stand, using a T-bar D spindle at 4 rpm.

The viscosities referred to above can be attained according to the present invention while maintaining a high ability to absorb exuded materials from the wound as can be demonstrated by means of a saline absorption test. That test comprises dispersing 2 grams of the dressing material in 20 ml of 0.9% aqueous NaCl solution. The dispersion is decanted into a 50 ml measuring cylinder. Once the dispersion has settled, the position of the phase separation is noted, from which the fluid absorption capacity can be calculated. It has been found that the dressing material of the invention can be made with a viscosity within the limits mentioned above, with a saline absorption of at least abut 200 ml of the solution per 100 grams of the wound dressing, preferably at least about 250 ml/100 gram, more preferably at least about 300 ml/100 gram. The absorption characteristics of the dressing material have been found to be enhanced as a result of a sterilization step in its preparation which involves exposing the material to heat and pressure. The viscosity that can be obtained in the material of the wound dressing material of the invention means that the material is capable of being manipulated conveniently over the area of the wound that is to be treated using the material. It also facilitates removal of the material from its packaging. In addition to facilitating manipulation, a relatively low viscosity can enable the tackiness of the material to be maintained relatively low, which reduces damage to the wound when the dressing is removed.

Control of the viscosity is one means of measurement which may be used to obtain a required ratio between copolymer and water in the gel mixture. However, other means may be adopted, to achieve desired water-absorption properties of the gel mixture, which effectively comprises required provision of a suitable "spreadable gel." This can range between "highly mobile" at one extreme to "very stiff" at the other extreme, and which can be obtained by variation of the proportion by weight of copolymer in the gel mixture between about 0.2% to about 6%. The particular weight proportion which may be selected can depend on the particular means adopted to dispense the gel mixture, with e.g. a highly mobile gel being suitable for introduction into a deep wound by a syringe, and a stiffer gel being suitable for extrusion e.g. from a squeezable sachet so as to be readily spread over the wound area.

In one preferred arrangement, the gel mixture may be stored in a squeezable sachet, and therefore the required properties of the gel mixture will be such that it can be readily squeezed from the sachet, and to be readily spread over the wound area.

The gel wound dressing of the invention has been found to be capable of providing suitable absorption characteristics, in particular towards solutions which are high in ionic strength, without any need to include aluminum ions. This can represent a significant advantage, in particular in situations in which the presence of aluminum ions can give rise to clinical complications.

Preferably, the gel wound dressing is formed from a mixture of particles of the copolymer and water, in which the distribution of particles is such that at least about 70% by weight, more preferably at least about 80%, especially at least about 90%, have a particle size of not more than about 100 μm. Preferably, the gel wound dressing is formed from a mixture of particles of the copolymer and water, in which the distribution of particles is such that at least about 60% by weight, more preferably at least about 70%, and especially at least about 85%, have a particle size of not more than about 75 μm. Preferably, the distribution of particles is such that not more than about 10% by weight, and more preferably not more than about 6%, have a particle size greater than about 100 μm. The particle size distribution can be determined using sieves with known mesh sizes, as is know.

It has been found that the use of particles of the copolymer whose size satisfies some or all of these conditions gives rise to materials with viscosities which make the copolymer suitable for use in the treatment of wounds, with the characteristics of a gel. The use of particles of the polymer with a size within these ranges has the advantage of making the material smoother without a granular texture. The smooth texture makes the material easier to spread appropriately over a wound that is to be treated. Also the gel usually will be clear i.e. transparent, so that the wound can be observed while the dressing is being applied.

Preferably, the gel wound dressing of the invention includes a component which reduces its tendency to dry out. This component may also act as a preservative. Examples of suitable materials include polyols, such as propane-1,2-diol and glycerol, or a mixture thereof. Preferably, the polyol component is present in the composition in an amount of at least about 100% by weight based on the weight of the copolymer, more preferably at least about 200%, specially at least about 300%, for example about 400%, and with advantage even up to 600%.

Preferably, the gel wound dressing of the invention includes at least one other active component. For example, the dressing might include an agent which inhibits or at least reduces the tendency for bacteria to colonize on the dressing. An example of a suitable such agent is a polyol such as propane-1,2-diol.

Examples of other active components that might be included in the dressing include anesthetic agents, hormonal compounds and lubricants, enzyme-containing compositions, antibiotics (such as metronidazole), collagen materials, cytokines (such as platelet derived growth factor, insulin-dependent growth factor, and transforming factored placentile growth factor), and elastin (preferably with fibrin and fibrinogen).

The copolymer used in the dressing is produced by reaction of a starch with a monoethylenically unsaturated carboxylic acid, or an ester or salt of such an acid. Examples of suitable components for the copolymer, together with the starch, include acrylic acid, methacrylic acid, lower carboxyl ($C_1$ to $C_4$) esters thereof and salts such as with elements of Groups I and II or ammonia. It is preferred that substantially all of the carboxyl groups in the copolymer are present as acid groups, or as salt or ester derivatives of acid groups.

A particularly preferred copolymer comprises at least about 50%, preferably at least about 70%, more preferably at least about 85%, for example, at least about 95%, of a salt of a starch grafted polyacrylate. Preferred salts include the sodium salt.

The copolymerization reaction between the starch and the acrylate component can be initiated by means of irradiation, for example using an electron beam, γ-radiation such as from a $Co^{60}$ source, or ultraviolet radiation. The reaction can also be initiated by means of a chemical initiator such as benzoyl peroxide, hydrogen peroxide or a salt such as a ceric salt.

Examples of suitable copolymers for use in the gel wound dressing of the invention are disclosed in British Patent No. 1,512,325, the subject matter of which is incorporated herein by this reference thereto. The British patent discloses water absorbing resin which comprises a copolymer of starch and a water soluble monomer such as acrylic acid or a derivative thereof. The resin is crosslinked as a result of a reaction with a crosslinking agent such as polyesters of unsaturated mono- or polycarboxylic acids with polyols (for example an ester of di-methacrylic acid with ethylene glycol). The resin is said to be suitable for absorbing fluids such as blood and urine, for example in diapers, sanitary towels and disposable dustcloths for kitchens. The disclosed resin can be applied in the form of a powder, in an aqueous dispersion, or by immersion of a substrate in a solution of the resin. The resin is said to be particularly suitable for use in diapers and sanitary towels.

The copolymer used in the dressing of the present invention will generally be crosslinked, so as to confer appropriate gel-like properties and viscosity on the dressing material. The crosslinks will preferably be internal crosslinks. It has been found that the use of a polymer which is crosslinked in this way gives rise to a smoother dressing material, which has advantages in use for example in terms of its ability to be spread.

The starch used to form the copolymer may be a natural starch such as potato starch, rice starch, tapioca starch or corn starch, or a modified or processed starch such as α-starch, dextrine and oxidized starch. Natural starches are particularly preferred.

The ratio by weight of the starch to the acid derivative component of the copolymer is preferably at least about 1, more preferably at least about 2, especially at least about 5, for example at least about 10. The ratio is preferably not more than bout $10^4$, more preferably not more than bout $10^3$, especially not more than about 100.

Suitable starch acrylate copolymers for use in the wound dressing of the invention are available from Hoechst Celanese under the trademark SANWET COS-915.

Preferably, the water that is present in the wound dressing gel is not more than about 60% of the total water absorbency of the copolymer, more preferably not more than about 5%, for example not more than about 3%.

The water absorbency of the copolymer is determined by immersing in deionized water a known weight of the gel (1 to 2 g) made to the exemplified formulation, contained in a sealed bag of hydrophilic polypropylene based non-woven fabric available from Scimat Limited under the trademark SCIMAT 700/13, and recording its weight change after 24 hours.

Prior to weighing, the surface of the bag is blotted to remove excess water and an empty bag is used as a control.

The total absorbency of the resin, measured in $ml.g^{-1}$ m is calculated as follows:

$$\text{Absorbency} = \frac{(\text{Water in gel}) + (\text{Water uptake in 24 h})}{\text{Resin in gel}}$$

However, the total water absorbency (T) can be difficult to measure in practice (due to variation between different batches of material), but tests carried out to date give the following desired parameters, wherein carrying out measurements for values from 900 to 1300 ml/g for pure water: In the formula:

$$R = \frac{Y}{xT} \times 100\%$$

in which R is the percentage proportion by weight of water present in the gel mixture relative to the total water absorbency of the copolymer in the gel mixture; T is the total water absorbency; X is the percentage by weight of copolymer in the copolymer/water gel mixture, and Y=amount of water added in the mixing stage.

For values of x=0.2 and t=900 and 1300 and Y=99.8, the values of R were found to be 55.4 and 38.4 respectively.

For value of X=6, and values of T=900 and T=1300 and Y=94, the values of R were found to be 1.74 and 1.21 respectively.

The value of x=0.2 gives a gel mixture which is very runny, or "highly mobile" as indicated earlier, whereas the value x=6.0 gives a gel mixture which is very stiff. These two values of x determine the range within which a suitable spreadable gel can be derived, to suit particular requirements. Therefore, suitable variation of the weight proportions of copolymer and water in the gel mixture may be selected, by experiment, within the range, to provide spreadable gel mixtures suitable for different requirements.

In a preferred example, which contains 3.5 parts copolymer and 75.5 parts water, then when T=900, R=2.4; and when T=1300, R=1.66, and Y=75.5.

Accordingly, in a particularly preferred range of proportion by weight of copolymer to water in a gel mixture of a gel wound dressing according to the invention, the relative proportion of water that is present in a particular sample, compared with the total water absorbency of the copolymer in the sample, lies in a range having a minimum value of up to 1.0%. The upper limit to the preferred range will be determined by experiment, but may go up to as high a value as r=60%.

If desired, for certain circumstances it may be advantageous to introduce substantial amounts of preservative e.g. a polyol into the gel mixture, (which replaces the amount of water required in the formulation of the gel), and this can then result in a lower value of R. By way of example, in a gel mixture of 3% polymer, 69% polyol, and 28% water, the value of R is reduced to 0.7. The invention therefore includes the possibility of including weight proportions in the gel mixture of polymer, preservative, and water such that R can be less than 1.0%, and down to at least 0.7%.

The gel dressing will generally be applied to a wound in a layer of thickness at least about 2 mm, preferably at least about 4 mm, for example at least about 5 mm. A dressing applied to certain wounds with this thickness can be left in situ for as much as seven days or more.

The dressing of the invention can be administered in a sachet from which it can be extruded through an opening, formed for example by means of a knife, by the application of pressure to the sachet.

The dressing can conveniently be administered in a syringe, from which it can be extruded in a controlled manner directly onto a wound so that it is appropriately located to ensure that the wetness of the wound is controlled.

The dressing can be administered in a porous container such as a pouch or sachet made of a material that is suitably porous to the fluids to be absorbed by the dressing when in place on the wound. Examples of materials that might be suitable for the sachet or pouch include paper based materials and organic materials such as polyamides and polyesters, especially in the form of a non-woven sheet.

The wound dressing of the invention can conveniently be applied directly to a wound. It is envisaged that, in most circumstances, the dressing will be changed after a period of, perhaps, hours or days, according to the condition of the wound, for example about 2 to 3 days (although shorter periods can be appropriate under certain conditions, for example when the amount of material exuding from the wound is high). When the dressing is to be changed, the gel-like characteristics of the dressing material facilitate its removal from the wound, and which may be assisted by irrigation, for example using a sterile saline solution.

It will generally be appropriate for a secondary dressing to be applied over the gel wound dressing, to retain it in place on a wound and to provide a degree of physical protection for the gel dressing. The nature of the secondary dressing will depend on the characteristics of the wound. For example, if the wound has eschar (dry crusty tissue) associated with it, a moisture vapor permeable dressing will be appropriate. If the wound is malodorous, an activated carbon dressing can be appropriate.

An appropriate secondary dressing can preferably exclude bacteria from the wound, retain the dressing material in place on the wound, and permit exchange of moisture with the atmosphere. Preferably, the dressing is transparent so that the wound can be inspected. Suitable secondary dressings are sold under the trademarks OPSITE and TEGADERM.

The invention also provides a method of making a gel wound dressing material, which comprises mixing a water absorbent copolymer of a starch and a monounsaturated carboxylic acid or an ester or salt thereof with a quantity of water, the proportions of the copolymer and water being such that the resulting mixture has gel properties.

Preferably, the method includes the step of sterilizing the gel wound dressing, for example by means of a heating step, optionally under pressure, or by irradiation if the materials of the dressing are not affected adversely by irradation. Unexpectedly the saline absorbency capacity of the sterilized gel is greater than that before sterilization.

The invention further provides a method of treating a wound which includes a step of applying a gel wound dressing of the type discussed above.

An example of a gel wound dressing will now be described. The dressing was made from a starch acrylate copolymer sold under the trademark SANWET COS-915. It is supplied by Hoechst Celanese. Typically it has a particle size distribution as follows:

| US SIEVE SIZE (mesh) | PARTICLE SIZE (μm) | SIZE DISTRIBUTION (wt %) | |
|---|---|---|---|
| | | Sample 1 | Sample 2 |
| +20 | >850 | 0.1 | 0.0 |
| −20/+140 | 100–850 | 1.9 | 0.3 |
| −140/+200 | 75–100 | 11.7 | 0.7 |
| −200/+325 | 45–75 | 38.8 | 43.7 |
| −325 | <45 | 47.6 | 55.0 |

The following components were mixed mechanically for 3 minutes until dispersed evenly (amounts expressed in parts by weight):

Starch acrylate copolymer 3.5
Propane-1,2-diol 20.0
Glycerol 1.0

75.5 parts by weight of water were added to the resulting mixture and the resulting mixture was stirred for a further 2 minutes until a homogeneous mixture was obtained.

The mixture was transferred to a shallow container and placed under a vacuum at room temperature to remove entrapped air.

Saline absorption was determined as follows: 2 g of gel was weighed into a beaker and 20 ml of 0.9% sodium chloride solution added. Once dispersed, the resulting dispersion was transferred to a 50 ml measuring cylinder. After settling, the volumes of the two layers was measured and the fluid absorbtion capacity calculated, as above.

Results for the formulation given in the example were as follows:

Absorbency before sterilization 325 ml/100 g gel
Absorbency after sterilization 400 ml/100 g gel Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A gel wound dressing which comprises a mixture of:
   (a) a water absorbent copolymer of a starch and a monounsaturated carboxylic acid or an ester or salt thereof, the copolymer being in the form of particles of which at least about 70% by weight have a size of not more than about 100 μm; and
   (b) water.

2. A wound dressing as claimed in claim 1, which includes a component which reduces the tendency of the dressing to dry out when exposed to atmosphere.

3. A wound dressing as claimed in claim 2, in which the said component is a polyol.

4. A wound dressing as claimed in claim 3, in which the said component comprises propane-1,2-diol.

5. A wound dressing as claimed in claim 2, in which the said component is present in an amount of at least 100% based on the weight of the copolymer.

6. A wound dressing as claimed in claim 1, which includes an agent which inhibits or at least reduces the tendency for bacteria to colonise on the dressing.

7. A wound dressing as claimed in claim 1, in which the distribution of the particles of the copolymer is such that at least about 80% have a particle size of not more than about 100 μm.

8. A wound dressing as claimed in claim 1 in which substantially all of the carboxyl groups in the copolymer are present as acid groups, or as salt or ester derivatives of acid groups.

9. A wound dressing as claimed in claim 1, in which the wound dressing comprises a spreadable gel mixture.

10. A wound dressing as claimed in claim 1, in which the proportion by weight of copolymer lies in the range from 0.2 to 6%.

11. A wound dressing as claimed in claim 1, in which, in the formula:

$$R = \frac{Y}{xT} \times 100\%$$

where R is the percentage proportion by weight of water present in the mixture relative to the total water absorbency of the copolymer, T is the total water absorbency, x is the percentage by weight of copolymer and Y is the amount of water in the mixing stage, R is at least 0.7%.

12. A wound dressing as claimed in claim 11, in which R is not more than 60%.

13. A wound dressing as claimed in claim 1, which is contained in a sachet from which the dressing can be extruded by application of pressure.

14. A wound dressing as claimed in claim 7 in which the distribution of the particles of the copolymer is such that at least about 90% have a particle size of not more than about 100 μm.

15. A gel wound dressing contained in a syringe, the gel wound dressing comprising a mixture of:
   (a) a water absorbent polymer of a starch and a monosaturated carboxylic acid or an ester or salt thereof, the copolymer being in the form of particles of which at least about 70% by weight have a size of not more than about 100 μm; and
   (b) water.

16. A wound dressing as claimed in claim 15, including a component which reduces the tendency of the dressing to dry out when exposed to the atmosphere.

17. A wound dressing as claimed in claim 15, wherein said component comprises a polyol.

18. A wound dressing as claimed in claim 15, wherein said component comprises propane-1,2-diol.

19. A wound dressing as claimed in claim 15, wherein said component is present in an amount of at least 100% based on the weight of the copolymer.

20. A wound dressing as claimed in claim 15, including an agent which inhibits or at least reduces the tendency for bacteria to colonize on the dressing.

21. A wound dressing as claimed in claim 15, wherein the distribution of the particles of the copolymer is such that at least about 80% have a particle size of not more than about 100 μm.

22. A wound dressing as claimed in claim 15, wherein substantially all of the carboxyl groups in the copolymer are present as acid groups, or as salt or ester derivatives of said acid groups.

23. A wound dressing as claimed in claim 15, wherein said wound dressing comprises a spreadable gel mixture.

24. A wound dressing as claimed in claim 15, wherein the proportion by weight of copolymer lies in the range from 0.2 to 6%.

25. A wound dressing as claimed in claim 15, wherein, in the formula:

$$R = \frac{Y}{xT} \times 100\%$$

where R is the percentage proportion by weight of water present in the mixture relative to the total water absorbency of the copolymer, T is the total water absorbency, x is the percentage by weight of copolymer and Y is the amount of water in the mixing stage, R is at least 0.7%.

26. A wound dressing as claimed in claim 15, wherein R is not more than 60%.

* * * * *